(12) United States Patent
Terwilliger et al.

(10) Patent No.: US 7,094,198 B2
(45) Date of Patent: Aug. 22, 2006

(54) DELIVERY SYSTEM AND METHOD FOR INTERSTITIAL RADIATION THERAPY USING SEED ELEMENTS WITH ENDS HAVING ONE OF PROJECTIONS AND INDENTATIONS

(75) Inventors: Richard A. Terwilliger, Southbury, CT (US); Gary A. Lamoureux, Woodbury, CT (US)

(73) Assignees: Worldwide Medical Technologies, LLC, Oxford, CT (US), part interest; Ideamatrix, Inc., Estes Park, CO (US), part interest ( * ) Notice: Subject to any disclaimer, the term of this patent is extended or adjusted under 35 U.S.C. 154(b) by 0 days.

(21) Appl. No.: 10/162,547

(22) Filed: Jun. 4, 2002

(65) Prior Publication Data
US 2003/0092958 A1 May 15, 2003

Related U.S. Application Data

(60) Provisional application No. 60/336,329, filed on Nov. 2, 2001, provisional application No. 60/360,299, filed on Feb. 26, 2002.

(51) Int. Cl.
*A61B 5/00* (2006.01)
(52) U.S. Cl. .............................................. 600/3; 600/8
(58) Field of Classification Search ................. 600/1–8
See application file for complete search history.

(56) References Cited

U.S. PATENT DOCUMENTS

| | | | |
|---|---|---|---|
| 1,578,945 A | 3/1926 | Withers | |
| 2,067,589 A | 1/1937 | Antrim | |
| 2,575,138 A | 11/1951 | Slaughter | |
| 3,351,049 A | 11/1967 | Lawrence | |
| 3,565,869 A | 2/1971 | DeProspero | |
| 3,636,956 A | 1/1972 | Schneider | |
| 3,752,630 A | 8/1973 | Takagi | |
| 3,811,426 A | 5/1974 | Culver et al. | |
| 4,052,988 A | 10/1977 | Doddi et al. | |
| 4,086,914 A | 5/1978 | Moore | |
| 4,167,179 A | 9/1979 | Kirsch | |
| 4,402,308 A | 9/1983 | Scott | |
| 4,416,308 A | 11/1983 | Simpson et al. | |
| 4,509,506 A * | 4/1985 | Windorski et al. | 600/8 |
| 4,697,575 A * | 10/1987 | Horowitz | 600/8 |
| 4,754,745 A | 7/1988 | Horowitz | |
| 4,784,116 A | 11/1988 | Russel, Jr. et al. | |
| 4,815,449 A * | 3/1989 | Horowitz | 600/7 |
| 4,936,823 A | 6/1990 | Colvin et al. | |
| 5,022,940 A | 6/1991 | Mehoudar | |

(Continued)

FOREIGN PATENT DOCUMENTS

EP         0 030 822 A2    6/1981

(Continued)

OTHER PUBLICATIONS

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

(Continued)

*Primary Examiner*—Samuel G. Gilbert
(74) *Attorney, Agent, or Firm*—Fliesler Meyer LLP (57) ABSTRACT

A delivery system and method for interstitial radiation therapy uses a seed strand composed of a plurality of radioactive seeds or encapsulated seeds having ends with projections or indentations connected by a polymer. The seed strand is axially stiff and radially flexible and is bioabsorbable in living tissue.

40 Claims, 4 Drawing Sheets

U.S. PATENT DOCUMENTS

| | | | |
|---|---|---|---|
| 5,339,812 A | | 8/1994 | Hardy et al. |
| 5,460,592 A | * | 10/1995 | Langton et al. ................. 600/7 |
| 5,713,828 A | * | 2/1998 | Coniglione ..................... 600/7 |
| 5,761,877 A | | 6/1998 | Quandt |
| 5,833,593 A | * | 11/1998 | Liprie ........................... 600/3 |
| 5,928,130 A | | 7/1999 | Schmidt |
| 5,938,583 A | | 8/1999 | Grimm |
| 6,010,446 A | | 1/2000 | Grimm |
| 6,039,684 A | * | 3/2000 | Ildstad et al. ................... 600/1 |
| 6,080,099 A | * | 6/2000 | Slater et al. .................... 600/8 |
| 6,099,457 A | | 8/2000 | Good |
| 6,132,677 A | | 10/2000 | Ohriner |
| 6,132,947 A | | 10/2000 | Honan et al. |
| 6,159,143 A | * | 12/2000 | Lennox ........................... 600/4 |
| 6,163,947 A | | 12/2000 | Coniglione |
| 6,200,255 B1 | * | 3/2001 | Yu ................................. 600/1 |
| 6,200,256 B1 | | 3/2001 | Weinberger |
| 6,248,057 B1 | * | 6/2001 | Mavity et al. .................. 600/3 |
| 6,264,599 B1 | * | 7/2001 | Slater et al. .................... 600/7 |
| 6,264,600 B1 | | 7/2001 | Grimm |
| 6,273,851 B1 | * | 8/2001 | Slater et al. .................... 600/8 |
| 6,283,911 B1 | * | 9/2001 | Keren ............................ 600/3 |
| 6,312,374 B1 | * | 11/2001 | von Hoffmann ............... 600/3 |
| 6,327,490 B1 | | 12/2001 | Spetz |
| 6,360,116 B1 | | 3/2002 | Jackson, Jr. et al. |
| 6,387,034 B1 | | 5/2002 | Lee |
| 6,398,709 B1 | | 6/2002 | Ehr et al. |
| 6,403,916 B1 | | 6/2002 | Spooner et al. |
| 6,428,504 B1 | | 8/2002 | Riaziat et al. |
| 6,438,401 B1 | | 8/2002 | Cheng et al. |
| 6,450,938 B1 | | 9/2002 | Miller |
| 6,450,939 B1 | * | 9/2002 | Grimm ........................... 600/8 |
| 6,474,535 B1 | | 11/2002 | Shanks et al. |
| 6,497,646 B1 | * | 12/2002 | Candelaria et al. ............ 600/7 |
| 6,500,109 B1 | | 12/2002 | Tokita et al. |
| 6,514,193 B1 | | 2/2003 | Kaplan |
| 6,537,193 B1 | | 3/2003 | Lennox |
| 6,539,247 B1 | * | 3/2003 | Spetz .......................... 600/427 |
| 6,549,802 B1 | | 4/2003 | Thornton |
| 6,572,525 B1 | | 6/2003 | Yoshizumi |
| 6,575,888 B1 | | 6/2003 | Zamora et al. |
| 6,595,908 B1 | * | 7/2003 | Loffler et al. .................. 600/7 |
| 6,626,817 B1 | | 9/2003 | Luth |
| 6,632,176 B1 | | 10/2003 | McIntire et al. |
| 6,656,106 B1 | | 12/2003 | Schmidt |
| 6,709,381 B1 | | 3/2004 | Munro, III |
| 6,746,661 B1 | | 6/2004 | Kaplan |
| 6,752,753 B1 | | 6/2004 | Hoskins et al. |
| 6,761,680 B1 | | 7/2004 | Terwilliger et al. |
| 6,786,858 B1 | | 9/2004 | Terwilliger et al. |
| 6,820,318 B1 | | 11/2004 | Terwilliger et al. |
| 2002/0188195 A1 | * | 12/2002 | Mills .......................... 600/431 |
| 2003/0084988 A1 | | 5/2003 | Terwilliger et al. |
| 2003/0092958 A1 | | 5/2003 | Terwilliger et al. |
| 2003/0191355 A1 | | 10/2003 | Ferguson |
| 2004/0015037 A1 | * | 1/2004 | Rapach et al. ................. 600/1 |
| 2004/0158117 A1 | | 8/2004 | Drobnik et al. |
| 2004/0158118 A1 | | 8/2004 | Drobnik et al. |

FOREIGN PATENT DOCUMENTS

| | | |
|---|---|---|
| EP | 0 030 822 B1 | 9/1983 |
| EP | 0 466 681 B1 | 1/1992 |
| WO | WO 00/64538 | 2/2000 |
| WO | WO 00/61229 | 10/2000 |

OTHER PUBLICATIONS

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

Webster's II New Riverside University Dictionary, p. 191, 1984.

Medi-Physics brochure entitled I-125 Seeds. No. 6711, Medi-Physics, Inc. Arlington Heights II. 60004, USA; Revised. Oct. 1999, 2 pages.

Medi-Physics brochure entitled I-125 Seeds. No. 7000; Medi-Physics, Inc. Arlington Heights II. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications" Http;//www.amershamhealth-us.com/products/index.htp?a=i&i=38; printed Nov. 19, 2003.

Amersham Health; OncoSeed™ (Iodine-125 Seeds) http://www.amershamhealty-us.com/oncoseed/; printed Nov. 19, 2003.

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

* cited by examiner

DELIVERY SYSTEM AND METHOD FOR INTERSTITIAL RADIATION THERAPY USING SEED ELEMENTS WITH ENDS HAVING ONE OF PROJECTIONS AND INDENTATIONS

CLAIM OF PRIORITY

This application claims priority from U.S. Provisional Patent Application No. 60/336,329, filed on Nov. 2, 2001, and this application claims priority from U.S. Provisional Patent Application No. 60/360,299 filed on Feb. 26, 2002 which applications are hereby incorporated herein by reference. This application claims priority from U.S. patent application Ser. No. 10/035,083 filed on Dec. 28, 2001 which is hereby incorporated herein by reference.

CROSS-REFERENCE TO RELATED APPLICATIONS

The following applications are cross-referenced and incorporated herein by reference:

U.S. Provisional Patent Application No. 60/360,241 entitled "Delivery System and Method for Interstitial Radiation Therapy Using Seed Strands Constructed With Preformed Strand Housing," by Terwilliger et al., filed Feb. 26, 2002. (WORLD-01000US2)

U.S. Provisional Patent Application No. 60/360,237 entitled "System for Manufacturing Interstitial Radiation Therapy Seed Strands," by Terwilliger et al., filed Feb. 26, 2002. (WORLD-01000US3)

U.S. Provisional Patent Application No. 60/360,272, entitled "Delivery System and Method for Interstitial Radiation Therapy Using Strands Constructed With Extruded Strand Housing," by Terwilliger et al., filed Feb. 26, 2002. (WORLD-01000US 4)

U.S. Provisional Patent Application No. 60/360,260 entitled "Delivery System and Method for Interstitial Radiation Therapy," by Terwilliger et al., filed Feb. 26, 2002. (WORLD-0100US0)

FIELD OF THE INVENTION

The present invention relates to systems and methods for delivering a plurality of radioactive sources to a treatment site.

BACKGROUND

Interstitial radiation therapy involves the placement of small radioactive seeds within therapeutic distance of a tumor site. Encapsulating radioactive material with low energy and short half life into a small seed for placement at the tumor site results in safe handling and reduces the risk of contamination of the patient or surrounding tissue with radiation.

Many individual seeds can be injected at the therapeutic site to provide constant irradiation of the tumor. Handling the many individual seeds necessary to treat a given patient is cumbersome because the seeds are small and must be loaded into a hollow needle for injection. During the implantation procedure, the seeds are injected or pushed into the tumor site as the needle is withdrawn from the site. The seeds are generally placed in a straight line relative to the tumor. Such individual seeds may tend to migrate along the residual needle track and change position relative to the tumor or treatment target. Seed migration may result in undesirable concentrations of seeds and a radiation overdose to some tissues, while also causing a reduced concentration of seeds in other areas and loss of therapeutic effect.

By connecting the seeds together by various structures prior to injection, the difficulties of seed handling and migration can be overcome. Connecting the seeds helps prevent migration around the tumor and subsequent changes in the radiation dose to the tumor.

Seeds can be connected by many structures. One method is to insert the seeds inside a nylon catheter and inject the catheter-seed combination into the treatment site. However, the nylon catheter can be difficult to place and the catheter ends are sewn next to the skin which provides a site for contamination or infection. Seeds are also placed by hand into a woven or braided absorbable suture. Loading the suture containing the seeds into the needle is time consuming. Also, the flexible suture braid tends to bend and clog the needle during implantation in the treatment site.

Horowitz (U.S. Pat. No. 4,697,575), incorporated herein by reference, describes seeds for interstitial use connected by interlocking members. The rigid needle-seed brachytherapy device of Horowitz is a non-deflecting member composed of rigid bioabsorbable polymers. The seeds are encapsulated within segments of the polymer and the segments are then physically interconnected or interlocked to form a needle. The segments have projections on one end and complimentary recesses on the opposite end. The non-deflecting seed needle maybe inserted into the treatment site alone or can be inserted into a hollow needle to assist implantation into the site. Use of the seed needle assembly is preferred because hollow needles can facilitate the transfer of cancer cells from a tumor treatment site. This configuration prevents any individual seed from migrating from the original implantation site. Also, the rigid strand can be inserted into the treatment site and broken or cut at the proper length. A rigid radioactive seed needle is, however, incapable of movement and remains fixed as the tumor or gland shrinks during the healing and treatment process.

SUMMARY OF THE INVENTION

The present invention overcomes the above disadvantages. The present invention provides a desirable configuration for radiation brachytherapy and includes a seed configuration that is rigid enough to facilitate insertion and prevent unwanted migration along needle tracks, and flexible enough to allow the connected seeds or seed strand to migrate relative to the tumor or gland as the tumor or gland shrinks during treatment.

Embodiments of seed strands of the invention include seed elements that comprise seeds with ends having indentations or projections, or encapsulated seeds that have ends having indentations or projections. The seed elements are connected with a material, preferably a bioabsorbable material that engages the indentations and/or projections to create a seed strand that is axially rigid and radially flexible.

DETAILED DESCRIPTION OF THE PREFERRED EMBODIMENTS

In accordance with an embodiment of the invention, a substantially axially semi-rigid and radially or laterally flexible elongated member made of material which is bioabsorbable in living tissue, is provided for insertion in tumors. Such an elongate member is flexible enough in the longitudinal plane or radial direction to (at an angle to the longitudinal axis of the seed strand) move with the tissues during the shrinkage of the tissue during treatment, yet axially rigid with enough column stiffness to allow for smooth implantation via a hollow needle. In the member or seed strand, a plurality of radioactive seeds are connected in the desired special relationship.

The seeds can be of various types having low energy and low half-life such as Iodine seeds, known as I-125 seeds, consisting of a welded titanium capsule containing iodine 125 absorbed on a silver rod, or Palladium 103 seeds. Examples of radioactive seeds used to manufacture the therapeutic element appear in Table 1 below.

TABLE 1

Seed Manufacturers and Common Types of Seeds.

| PART NUMBER | MANUFACTURER | SEED NAME |
|---|---|---|
| IODINE[125] | | |
| 80040-A | Amersham 6702 | OncoSeed |
| 80040-B | Amersham 6711 | RAPID Strand |
| 80040-C | North American Scientific | IoGold |
| 80040-D | Best Industries | BEST Iodine-125 |
| 80040-E | Bebig | Symmetra |
| 80040-F | Mills Biopharmaceuticals | ProstaSeed |
| 80040-G | Syncor | PharmaSeed |
| 80040-H | International Isotopes | IsoStar |
| 80040-I | Implant Sciences | I-Plant |
| 80040-J | International Brachytherapy | InterSource-125 |
| 80040-K | Source Tech | STM1251 |
| 80040-L | DRAXIMAGE, Inc. | BrachySeed |
| PALLADIUM[103] | | |
| 80035-A | North American Scientific | Pd Gold |
| 80035-B | Theragenics | Theraseed 200 |
| 80035-C | Best Industries | BEST Palladium-103 |
| 80035-D | International Brachytherapy | InterSource 103 |

Additionally, seeds can be manufactured using iridium 192, cesium 131, gold 198, yttrium 90 and phosphorus 32. Further radioactive isotopes used to manufacture seeds are not limited to these examples, but can include other sources of different types of radiation. In addition it is to be a understood that other types of seeds can be used. In particular, seeds such as those described in U.S. Pat. No. 6,248,057, which patent is incorporated herein by reference and which is entitled Absorbable Brachytherapy and Chemotherapy Delivery Devices and Methods, can be used with the present invention. These seeds include radiation delivery devices, drug delivery devices, and combinations of radiation and drug delivery devices in the form of beads, seeds, particles, rods, gels, and the like. These particular seeds are absorbable. The radiation element or drug delivery element is contained within, for example, absorbable polymers such as those listed below or in the above-referenced patent. In such seeds, the bioabsorbable structure can have a predefined persistence which is substantially longer than a half-life of the radioactive element contained in the bioabsorbable structure. The above bioabsorbable seeds can be used in the same manner as the other seeds described herein with respect to the invention.

The substantially axially rigid, and radially flexible elongated member can be made of any of the natural and/or synthetic biocompatible and bioabsorbable materials. Natural and synthetic polymers and copolymers can be used. Examples of synthetic bioabsorbable polymer materials are the polymers and copolymers of glycolide and lactide, polydioxanone and the like. Such polymeric materials are more fully described in U.S. Pat. Nos. 3,565,869, 3,636,956, 4,052,988 and European Patent Application 30822 all of which are incorporated herein by reference. Specific examples of bioabsorbable polymeric materials that can be used to produce the substantially axially stiff and radially flexible elongated member of embodiment of the present invention are polymers made by ETHICON, Inc., Somerville, N.J., under the trademarks "MONOCRYL" and "MAXON" which material is incorporated herein by reference.

Table 2 below provides examples of polymers (and manufacturers) suitable for use in producing embodiments the therapeutic member of the invention. A further discussion of such biodegradable polymers can be found in an article by John C. Middleton and Arthur J. Tipton entitled "Synthetic Biodegradable Polymers as Medical Devices," published March 1998 in Medical Plastics and Bio-materials which article is incorporated herein by reference.

TABLE 2

Biodegradable polymers, properties and degradation time.

| POLYMER | MELTING POINT (° C.) | GLASS-TRANSITION TEMP (° C.) | MODULUS (Gpa)[a] | DEGRADATION TIME (MONTHS)[b] |
|---|---|---|---|---|
| PGA | 225–230 | 35–40 | 7.0 | 6 to 12 |
| LPLA | 173–178 | 60–65 | 2.7 | >24 |
| DLPLA | Amorphous | 55–60 | 1.9 | 12 to 16 |
| PCL | 58–63 | (−65)–(−60) | 0.4 | >24 |
| PDO | N/A | (−10)–0 | 1.5 | 6 to 12 |
| PGA-TMC | N/A | N/A | 2.4 | 6 to 12 |
| 85/15 DLPLG | Amorphous | 50–55 | 2.0 | 5 to 6 |
| 75/25 DLPLG | Amorphous | 50–55 | 2.0 | 4 to 5 |
| 65/35 DLPLG | Amorphous | 45–50 | 2.0 | 3 to 4 |
| 50/50 DLPLG | Amorphous | 45–50 | 2.0 | 1 to 2 |

[a]Tensile or flexural modulus.
[b]Time to complete mass loss. Rate also depends on part geometry.

The final hardness of the polymer of elongate member should preferably be in a range from 20 to 80 durometer and more preferably in the range of 20–40 durometer. The bioabsorbable material should preferably be absorbed in living tissue in a period of time of from about 70 to about 120 days, but can be manufactured to be absorbed anywhere in a range from 1 week to 1 year, depending on the therapeutic plan for each specific patient. Preferably the bioabsorbable material is selected to absorb about when the half-life of the radioactive seeds is reached.

Figure 1A:
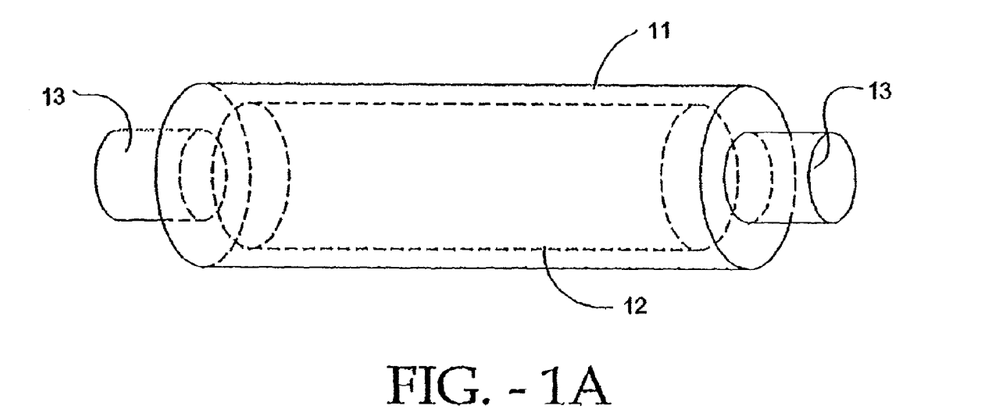
FIGS. 1A–1C depict enlarged side views of a radioactive seed within a capsule depicting various end geometry configurations.

In FIG. 1A, an encapsulated radioactive seed 12 is depicted. The capsule 11 having seed 12 is preferably composed of a bioabsorbable polymer as identified above which is preferably radio-opaque. The polymer used to encapsulate the radioactive seed 12 is, in this particular embodiment, very rigid and non-flexible. The radioisotope for the seed 12 is typically a low energy, short half-life isotope such as though listed in Table 1. The radioactive emissions penetrate the capsule 11 to the surrounding tissue or tumor. A projection 13 from the exterior of the capsule 11 may be formed of the same material as the capsule 11. A capsule 11 with identical outwardly directed projections 13 extending from each end of the capsule 11 is shown in FIG. 1A. Although the projections 13 pictured are cylindrical in shape, the present invention is not limited to cylindrical projections 13. As described below, in order to assemble a seed strand, the capsules 11 are spaced within a jig and liquid polymer is flowed into the spaces between the capsules 11, surrounding the projections, and then allowed to harden. Alternatively, suture material made of the polymer can be inserted into the space between neighboring capsules or wrapped around the projections 13 of neighboring capsules and heated. The polymer suture then melts and adhere strongly to the capsules, providing a radially flexible, yet axially rigid strand of seeds. The encapsulated seeds of FIGS. 1B and 1C can be similarly assembled. It is to be understood that the spacing between capsules 11 can vary in accordance with a prescription plan set forth below. Thus the spacing between any two capsules 11 can be made to a custom length per the prescription plan.

Figure 1B:
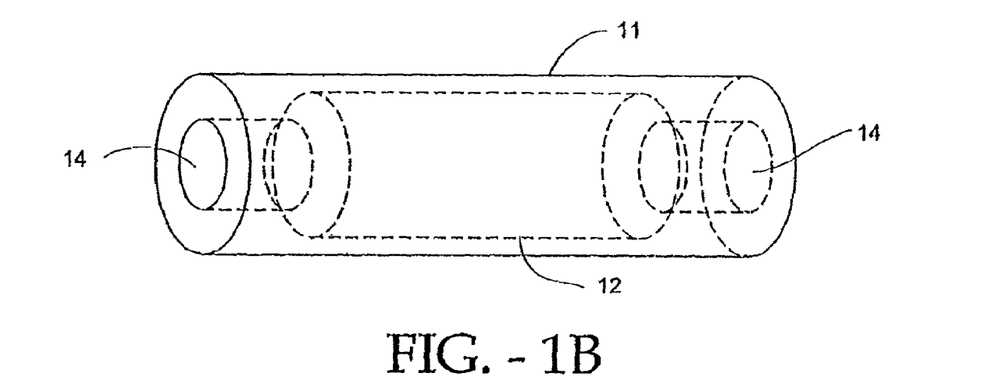

FIG. 1B depicts another embodiment of the current invention. The capsule 11 is composed of a polymer as identified above. In this embodiment, the radioactive seed 12 may contain or support any low energy, short half-life isotope, such as those in Table 1. The ends of the capsule 11 have indentations 14 formed into the capsule. Although the indentations 14 are pictured as cylindrical, they may be many shapes. The indentations 14 serve as an anchoring point for polymer used to connect the seed capsules 11 into a seed strand for implantation. It is to be understood that the spacing between capsules 11 can vary in accordance with a prescription plan set forth below. Thus the spacing between any two capsules 11 can be made to a custom length per the prescription plan. The seed strand can be manufactured as further described below.

Figure 1C:
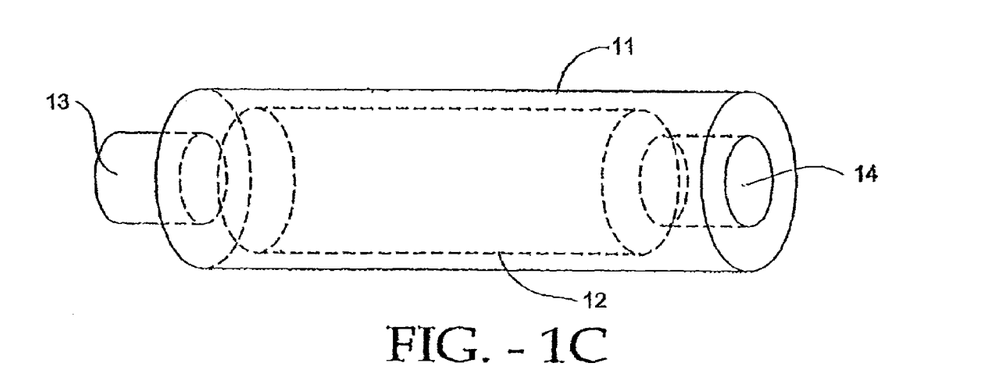

FIG. 1C depicts yet another embodiment of the present invention. The capsule 11 may be composed of a bioabsorbable polymer that is very hard and rigid. A radioactive seed 12 is contained within the capsule 11. A low-energy, short half-life radioisotope is contained within the seed 12. In this embodiment, the ends of the capsule 11 have different structures. The first end is an indentation 14, while the second end is a projection 13. While the indentation 14 and projection 13 pictured are cylindrical in shape, the present invention is not so limited. The projection 13 and indentation 14 ends can be aligned in any manner and used as anchoring structures to connect seed capsules 11 to each other by use of a polymer, as further described below. It is to be understood that the spacing between capsules 11 can vary in accordance with a prescription plan set forth below. Thus the spacing between any two capsules 11 can be made to a custom length per the prescription plan.

Figure 2A:
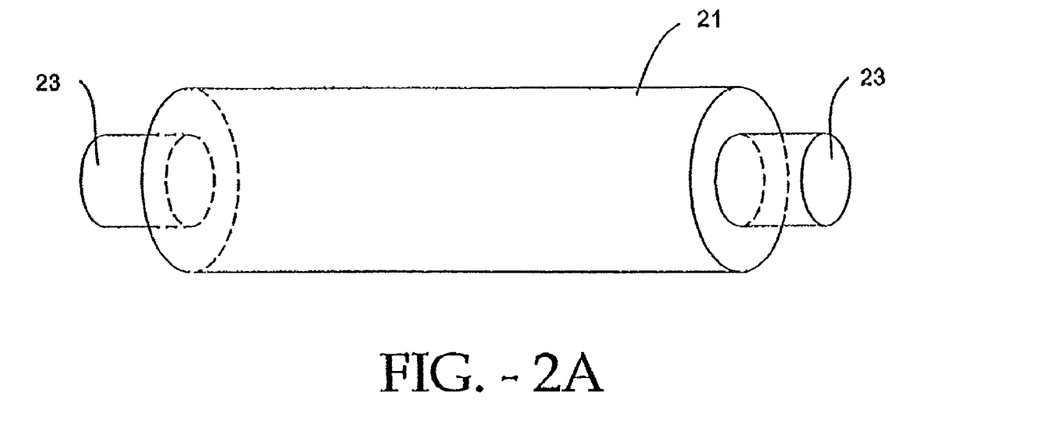
FIGS. 2A–2C depict enlarged side views of a radioactive seed depicting various end geometry configurations.

FIG. 2A depicts a radioactive seed 21 without a capsule. The seed 21 can contain or be coated with any low energy, short half-life isotope, such as those found in Table 1. The radioisotope is not limited to the isotopes in Table 1. The composition of the seed 21 maybe of titanium or any radio-opaque composition. If a polymer is used to make the seed 21, it may be made of a biocompatible polymer that is rigid. If a bioabsorbable compound is used to make the seed 21 it can degrade after the isotope emissions have reached appropriate levels. The structure of the seed 21 may be generally cylindrical, but is not limited in this way. FIG. 2A shows a seed 21 having projections 23 on each end. Although the projections 23 pictured are cylindrical, they are not limited to this shape.

Figure 2B:
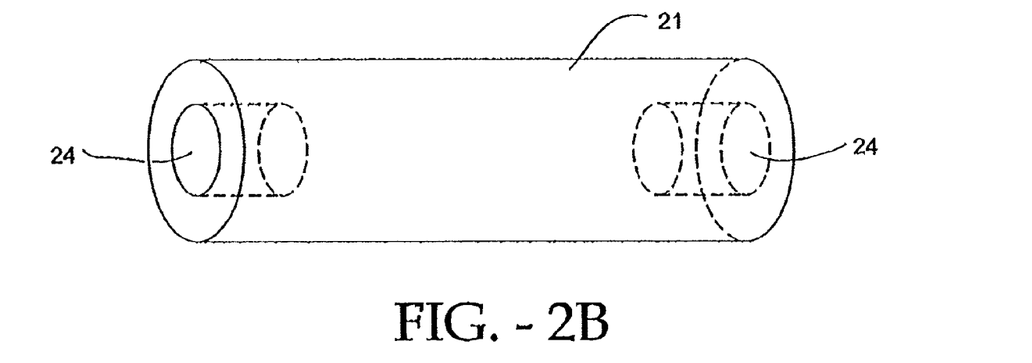

FIG. 2B shows another embodiment of the present invention. Depicted is a radioactive seed 21 with indentations on each end. The seed 21 maybe composed of titanium or any other radio-opaque metal or a rigid biocompatible polymer. Although the preferred embodiment would have a cylindrical shape, the present invention is not so limited. The radioactive seed may include any short half-life, low energy isotope shown in Table 1, but is not limited to these isotopes. The ends of the seed have indentations 24. Although the indentations 24 pictured are cylindrical in shape, the present invention is not so limited.

Figure 2C:
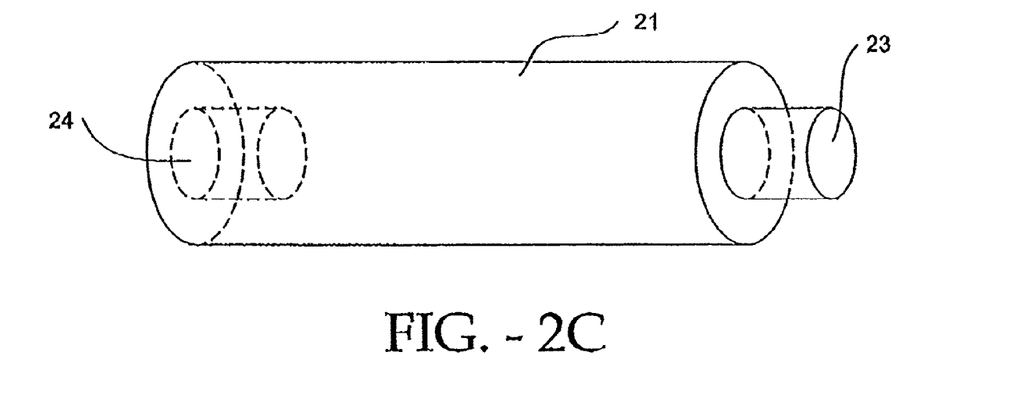

FIG. 2C is yet another embodiment of the present invention. The radioactive seed 21 can contain any low energy, short half-life isotope and be composed of titanium or another radio-opaque metal or a rigid biocompatible polymer. The radioactive seed pictured has two ends, one end has a projection 23 and one has an indentation 24. The end structures are pictured as cylindrical in nature, but are not so limited. With respect to the embodiments of FIGS. 2A, 2B, 2C, as described herein, the spacing between any pair of seeds can be custom set per a prescription plan.

Figure 3A:
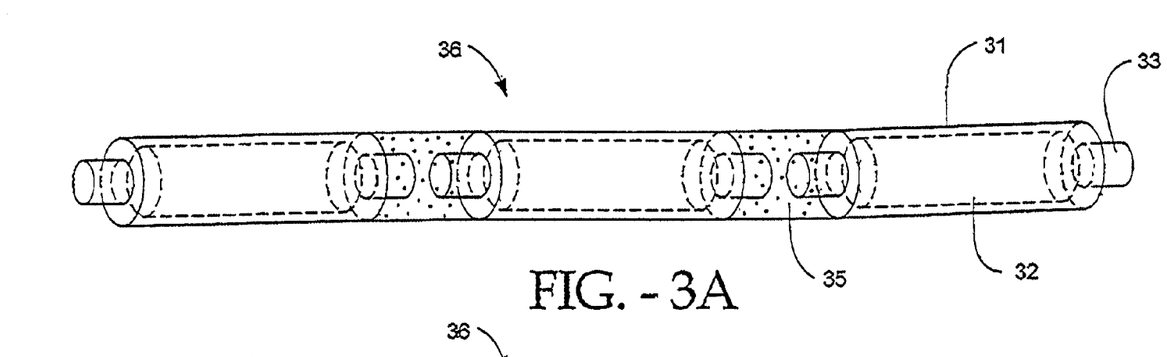
FIGS. 3A–3C depict enlarged side views of encapsulated radioactive seeds connected by a polymer.

FIG. 3A depicts a partial diagram of a therapeutic element or seed strand 36. Radioactive seeds 32 are encased in capsules 31 with projections 33 on the ends of the capsule 31 as depicted in FIG. 1A. Although the embodiment pictured depicts cylindrical capsules, seeds and projections, the present invention is not so limited. In between each capsule 31 is polymer 35. The seed strand connected by polymer 35 can be formed by positioning the seeds 32 within their capsules 31 at specific intervals within a jig and flowing heated, liquid polymer into the spaces between the seeds. The polymer can be selected from the above with preferable a durometer range as specified above. Alternatively, a polymer suture material composed of the polymer may be attached to the projections 33 on the ends of the capsules and heated and melted, forming a solid member between the capsules that is axially rigid, yet radially flexible. Preferably the polymer is one selected from the table above and is within the durometer ranges given above. Also, suture material comprised of a bioabsorbable material, such as from the above tables, can be wound around the projections and heated to fuse the capsules 31 together.

Figure 3B:
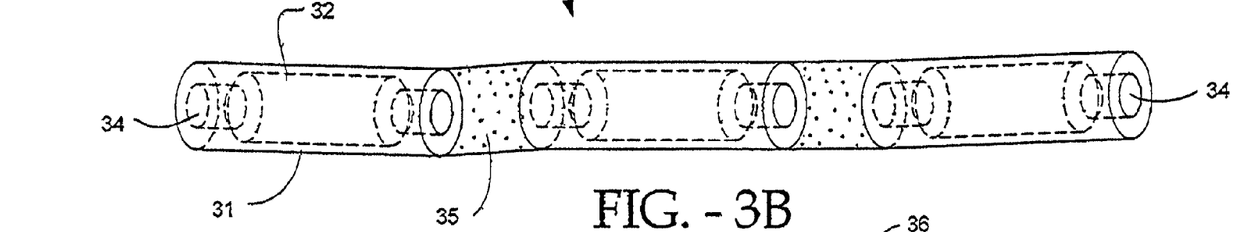

In another embodiment, FIG. 3B depicts a therapeutic element or seed strand 36 composed of radioactive seeds 32 within capsules 31 as depicted in FIG.1B. The capsules 31 having an alternative end structure. The end structure in FIG. 3B includes indentations 34 into the structure of the capsule. Although the indentation 34 pictured has a cylindrical shape, the present invention is not so limited. The material 35 that connects the capsules to form a therapeutic element or seed strand is preferably a polymer as identified in the above table and with the above-identified durometer range that is flowed into the area between the capsules 32 after the capsules are placed in a jig with specific spacing between the capsules 32. The heated, liquid polymer then cools and solidifies making a therapeutic strand of capsules 32 containing radioactive seeds 31 that is axially rigid, yet radially flexible. Alternatively, suture material made from the polymer can be inserted into the indentations 34 on the capsules and heated and melted. In either embodiment, the resulting therapeutic element consists of a strand 36 of radioactive elements interspersed that is axially rigid, yet radially flexible.

Figure 3C:
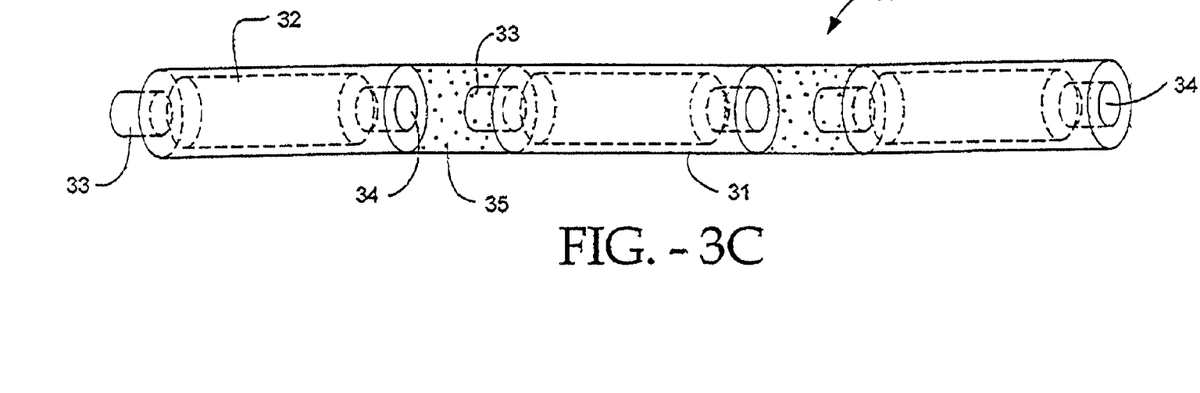

In yet another embodiment, FIG. 3C depicts radioactive seed 32 elements in a capsule 31 as depicted in FIG. 1C connected with a polymer 35. In this figure, each of the capsules has an indentation 34 at one end and a projection 33 at the other end. Although each capsule 31 is depicted with a cylindrical projection 33 at one end and a cylindrical indentation 34 at the other end, the present invention is not so limited by shape of the projection 33 or indentation 34. The capsules 31 can be placed in a jig and heated liquid polymer, or any other material, flowed between the capsules in order to make a seed strand. Alternatively, a suture 35 made of the above-identified polymer can be inserted into the indentation 34 and attached to the projections 33. The polymer is then heated and serves as a connection between the capsules 31. With respect to the embodiments of FIGS. 3A, 3B, 3C, as described herein, the spacing between any pair of capsules can be custom set per a prescription plan.

Figures 4A, 4B:
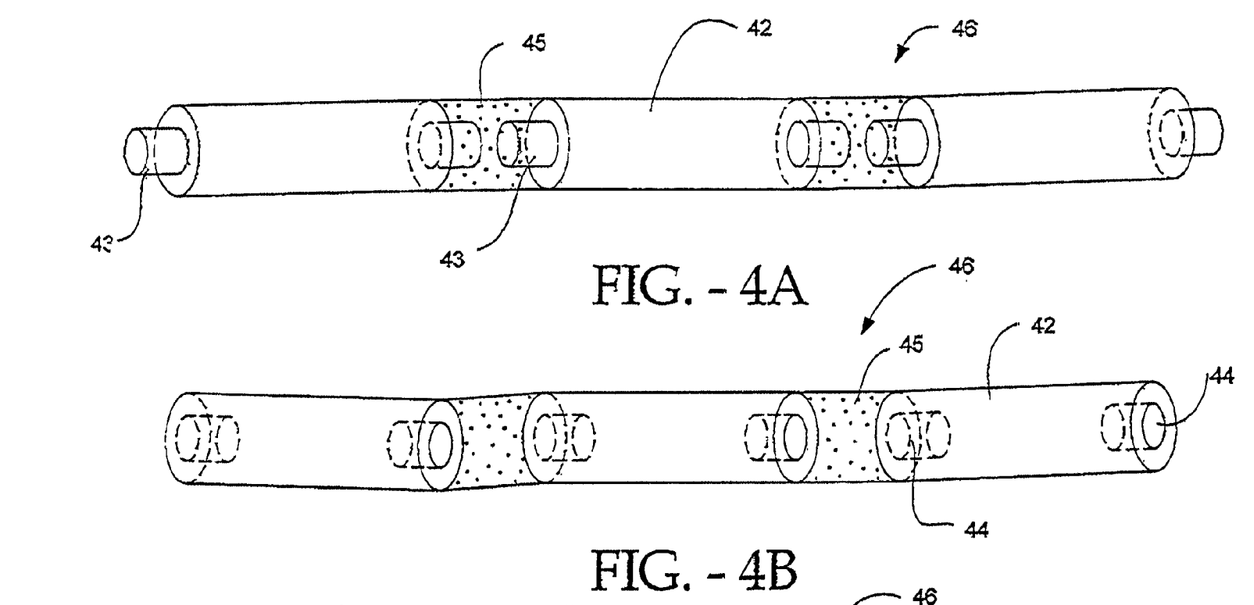
FIGS. 4A–4C depict enlarged side views of radioactive seeds connected by a polymer.

FIG. 4A depicts a therapeutic element or seed strand 46 composed of radioactive seeds 42 without capsules as depicted in FIG. 2A. The seeds 42 pictured have ends with projections 43. These projections 43 are shown as cylindrical, but the present invention is not so limited. Between the seeds 42 is a material 45. This material can be preferably a polymer as shown in Table 2. In order to make seed strands, the seeds 42 are placed in a jig and liquid polymer flows between the seeds. Alternatively, a suture made of the same polymer can be attached to the projections and melted, thereby making a seed strand 46.

FIG. 4B depicts yet another embodiment of a therapeutic element or seed strand composed of radioactive seeds 42 without capsules as shown in FIG. 2B. The seeds 42 can be constructed of titanium or any radio-opaque metal or a rigid polymer, including those listed in Table 2. Although the seeds 42 pictured are cylindrical in shape, the present invention is not so limited. The seeds 42 may contain or be coated with any low energy, short half-life isotope, including those listed in Table 1. The seeds 42 pictured have ends with indentations 44. These indentations 44 are shown as cylindrical, but the present invention is not so limited. Between the seeds 42 is a material 44 that is axially rigid and radially flexible. This material 45 can be a polymer as shown in Table 2. To manufacture the seed strand, the seeds 42 are placed in a jig, and liquid polymer flowed between the seeds 42 and into the indentation 44. As the polymer solidifies, a seed strand 46 is formed. Alternatively, a suture made of the polymer can be inserted into the indentations 44 and melted, forming a solid polymer connection between each seed 42 in the therapeutic element strand 46.

Figure 4C:
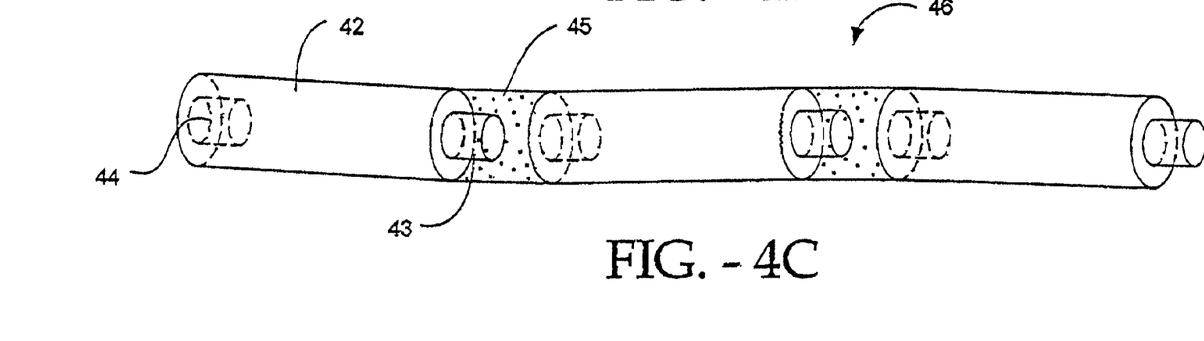

FIG. 4C depicts another embodiment of a therapeutic element 46 composed of radioactive seeds 42 without capsules as shown in FIG. 2C. The seeds 42 can be constructed of titanium or any radio-opaque metal or a rigid polymer, including those listed in Table 2. Although the seeds 42 pictured are cylindrical in shape, the present invention is not so limited. The seeds 42 may contain or be coated with any low energy, short half-life isotope, including those pictured in Table 1. The seeds 42 pictured have two ends, one with a projection 43 and one with an indentation 44. These projections 43 and indentations 44 are shown as cylindrical, but the present invention is not so limited. Between the seeds 42 is a material 45 that is used to make a seed strand 46 that is axially rigid and radially flexible. This material 45 can be a polymer as shown in Table 2. In order to manufacture the seed strand, the seeds 42 are placed in a jig and liquid polymer flowed between the seeds 42, around the projection 43 on one end of a seed and into the indentation 44 in a neighboring seed end. As the polymer solidifies, a seed strand 46 is formed that is axially rigid and radially flexible. Alternatively, a suture strand of the material 45 can be inserted into the indentations 44 and wrapped around the projection 43, then melted, forming a solid polymer connection between each seed in the therapeutic element strand 46. With respect to the embodiments of FIGS. 4A, 4B, 4C as described herein, the spacing between any pair of seeds can be custom set per a prescription plan.

Manufacturing Process

All of the above seed strands can be manufactured using the following process. The or strand can be fashioned with a manufacturing method known as insert or compression molding. The radioactive seeds and/or polymer encapsulated seeds are placed into a fixture that spaces the seeds at the appropriate intervals in a cavity that is shaped to the desired final dimensions of the elongated member. All the spacings can be of different lengths, if the preoperative therapeutic plan so specifies. The width of the fixture used in molding can be made larger than the width of the seeds by varying amounts. This allow for the polymer to adhere to the ends geometry of the seeds and further encapsulate the exterior of the full length of the seed not at all or to varying thicknesses. The polymer is introduced into the mold at a temperature that is above the melt point of the polymer. The polymer flows around the seeds within the cavity, surrounds the seeds and fills in the spaces between the seeds. After the mold has cooled, it is disassembled, and the finished elongated member is removed. Because the polymer flows at temperatures significantly greater than 250° F., the therapeutic element can easily be steam sterilized before implantation.

As specified above, the member connecting radioactive seeds maybe fashioned using compression molding techniques. Compression molding forms the molded piece in a two-part mold where the polymer material is placed within the cavities of the mold in a liquid state. The seeds are placed in position within the cavities filled with the polymer and the mold is closed and compressed, then cooled to form a piece that conforms to the shape of the closed cavity.

The manufacturing process also can make the member echogenic. In the case of the molding of the elongated member, air can be entrapped in the polymer material. During the cooling stage of the molding process, the mold is placed in a vacuum chamber and the air in the chamber is evacuated. This causes the entrapped air in the mold to come out of solution from the polymer, and as the mold cools, this air is entrapped within the cooling polymer in the form of minute bubbles suspended in the plastic.

Air is a strong reflector of ultrasound energy, since the inherent impedance of air is many times greater than body tissue. When the elongated member is introduced into the body and imaged with ultrasound, the elongated member is clearly visible in the resulting image, and is thus echogenic.

The resulting elongated member is now a single solid monofilament of the polymer with the seeds spaced relative to the monofilament connectors at the appropriate intervals. The member is generally very axially flexible such that it can be bent back upon itself in a circle without kinking. However, the member has sufficient column strength along its longitudinal axis so that the member can be urged out of a hollow needle without the member folding upon itself. Again, the intervals can be selected to be any distance or combination of distances that are optimal for the treatment plan of the patient.

Based on the above it is evident that the present invention provides for an embodiment having seed connectors comprised of a biodegradable polymer which connect a plurality of spaced radioactive therapeutic seeds. The seeds can be spaced in custom manner so that each member or strand is designed for the particular patient. That is to say that the spacing between each seed pair in a strand or member can be different for each seed pair. Further each individual strand can have an entirely different seed spacing pattern than the next strand or member. Characteristically or typically for a surgical procedure, up to twenty-five of such strands or members are used to encircle the organ or tumor that is affected.

Further such an arrangement provides for a strand or member that is stiff along its longitudinal axis. That is to say that the strand or member has column strength or stiffness while the strand or member is flexible in the direction which is radial or substantially perpendicular to the longitudinal axis. Accordingly the strand or member in a preferred embodiment is able to bend back upon and touch itself, when formed in a characteristic length.

In other embodiments, the strand or member can be made with the incorporation of drugs and/or hormones and/or other therapeutics which are embedded in or formed in the polymer and/or seeds. Thus the embodiment of the invention can deliver not only radioactive seeds, but such therapeutic drugs, hormones and other therapeutic devices. In addition the strand or member can deliver heated seeds such as provided by ATI Medical. Then seeds can be preferably heated to from about six (6) degrees centigrade to about seventy (70) degrees centigrade prior to being inserted into a patient in a preferred embodiment. ATI Medical is located at (www.ATImedical.com), and reference to such heated seeds is incorporated herein by reference.

It should be understood that other seed types can be used with the present invention. Thus for example in addition to the above encapsulated seeds, seeds which are made of radioactive or coiled wires can be embedded in the polymer and be within the spirit and scope of the invention. These seeds can be individual seeds which are spaced within a polymer or a continuous seed which extends the length of the strand or member.

Further to the invention, as discussed above, it should be understood that the strand or member can be made echogenic by the incorporation of, for example, air bubbles 32 in the polymer spaces between the seeds, as can be seen in FIGS. 3A–3C and FIGS. 4A–4C. These air bubbles or pockets can be formed in the polymer in ways identified above and other ways known to one of skill in the art.

According to the above, the advantages of the improved delivery system submitted of the present invention are:
1. The substantially axially stiff and radially flexible member allows controlled placement of the plurality of radioactive seeds that are connected and positioned in a predetermined array in the member without migration of the individual radioactive seeds during the time the seeds are treating the tumor.
2. The fixed linear positioning of the seeds minimizes "hot" and "cold" radiation spots due to undesirable movement of the seeds.
3. The axial stiffness of the elongated member allows the elongated member to be urged out of the needle as the needle is withdrawn, without the member jamming in the needle, by collapsing or expanding as the needle is withdrawn from the tumor site.
4. The longitudinal flexibility of the elongated member allows locational accuracy to be maintained as the gland shrinks to pre-procedural size, as the swelling that occurs during tissue disruption and needle manipulation recedes.
5. Increased speed of implant resulting in reduced surgical time and health care provider radiation exposure.

Method of Delivering Customized Strands and/or Members per a Therapeutic Prescription As is known in the industry, there is software which can be used to provide branchytherapy treatment planning guides which are customized for each individual patent. Such software is provided by Rossmed which is located at Ross Medical, 7100 Columbia Gateway Drive, Suite 160, Columbia, Md. 21046. This particular software, which is incorporated herein by reference, is known as the Strata suite, which software helps physicians to develop and visualize low dose rate brachytherapy treatment plans for treating malignant tumors in human tissue. The treatments entail the use of radioactive seed sources which are implanted adjacent to the malignant tissue. The Strata software uses imaging to create a three dimensional reconstruction of the patient's anatomy. The software is able to plan the placement of the seeds within the target. The radiation dose that is delivered to the target can be computerized and visualized using the software. The software can then specify an optimal number of strands or members along with optimal seed dosages and spaces between seeds or encapsulated seeds. At times the loading plans so specified cannot be optimized by the physician in preparing the seed and spacer loads for the needles, as the spacers come in only predefined lengths.

Accordingly with the present invention, the software can be used to prepare a prescription which optimizes the number of members or strands, and placement and spacing of seeds or encapsulated for each of the strands or members. This optimization plan can then be sent to a manufacturing site. By using the techniques of an embodiment of the present invention, an optimized strand or member can be created with the specified number of seeds and the specified distances between each seed pair. Once this prescription is filled at the manufacturing site, the custom strand or member can be sent back to the physician for treatment of the patient. With such an arrangement, radiation patterns can be optimally established for the treatment of each patient. Further the preparation time for the physician is greatly diminished as the physician does not have to hand assemble and hand load the seeds and spacers into the needle.

Further even if the physician were to use a prescription provided by the above software, with prior manufacturing techniques, the physician would only receive from the manufacturing facility a strand or member which has seeds spaced at predefined intervals, which are the lengths or the pre-manufactured spacers. Accordingly optimal treatment as provided by the custom strands or members manufactured according to the present invention could not be realized.

Additional aspects, objects and advantages of the invention can be obtained through a review of the appendant claims and figures. It is to be understood that other embodiments can be fabricated and come within the spirit and scope of the claims and the invention.

What is claimed is:
1. A method for manufacturing therapeutic elements, comprising the steps of:
    selecting a plurality of radioactive seed elements, each having a first end and a second end, wherein the first end has one of an indentation and a projection and the second end has one of an indentation and a projection;
    arranging said plurality of radioactive seed elements end-to-end with a desired spacing in between adjacent radioactive seed elements, said spacing customized to a patient's treatment prescription;
    introducing a liquid polymeric material into the spacing between the adjacent radioactive seed elements so that the liquid polymeric material engages said projections and said indentations of said first ends and said second ends without completely encapsulating said radioactive seed elements; and allowing said liquid polymeric material to solidify in engagement with said ends, thereby connecting said ends of said plurality of radioactive seed elements to form a treatment strand, said treatment strand customized to the patient's treatment prescription without the use of pre-fabricated spacers and said treatment strand having said plurality of radioactive seed elements connected by segments of the solidified polymeric material.

2. The method of claim 1 wherein the introducing step further comprises using a co-polymer as the polymeric material.

3. The method of claim 1 wherein the introducing step further comprises using a natural bio-compatible material as the polymeric material.

4. The method of claim 1 wherein the introducing step further comprises using a synthetic bio-compatible material as the polymeric material.

5. The method of claim 1 wherein the introducing step further comprises using a natural bio-absorbable material as the polymeric material.

6. The method of claim 1 wherein the introducing step further comprises using a synthetic bio-absorbable material as the polymeric material.

7. The method of claim 1 wherein the introducing step includes forming the treatment strand that has a substantially constant diameter.

8. The method of claim 1 wherein the introducing step includes forming the treatment strand having a diameter substantially similar to a diameter of the plurality of said radioactive seed elements.

9. The method of claim 1 further comprising, before the introducing step, the step of selecting a polymeric material, which material, after the allowing step, provides said treatment strand with sufficient radial flexibility to maintain locational accuracy of said plurality of radioactive seed elements relative to a tumor target as said tumor target shrinks in size.

10. The method of claim 1 wherein the introducing step further comprises ensuring that the thickness of said treatment strand around said plurality of radioactive seed elements is sufficient to decrease normal tissue necrosis from a high local dose of radiation.

11. The method of claim 1 further comprising, before the introducing step, the step of selecting a polymeric material so that said treatment strand is longitudinally flexible.

12. The method of claim 1 further comprising the step of incorporating a hormone into said polymeric material.

13. The method of claim 1 further comprising the step of incorporating a therapeutic agent into said polymeric material.

14. The method of claim 1 further comprising the step of incorporating a hormone into said plurality of radioactive seed elements.

15. The method of claim 1 further comprising the step of incorporating a therapeutic agent into said plurality of radioactive seed elements.

16. The method of claim 1 further comprising the step of providing the plurality of radioactive seed elements wherein said plurality of radioactive seed elements contains at least one of a compound and an element that emits photonic radiation having a low energy and a short half-life.

17. The method of claim 1 wherein the selecting step further comprises the step of selecting said plurality of radioactive seed elements contains at least one isotope selected from the group consisting of iodine 125, palladium 103, iridium 192, cesium 131, gold 198, yttrium 90, and phosphorus 32.

18. The method of claim 1 further comprising selecting said polymeric material that is absorbed by living tissue within about 70 to 120 days after implant.

19. The method of claim 1 further comprising selecting said polymeric material that is substantially absorbed by living tissue at substantially the same time as the half-life of the plurality of radioactive seed elements is reached.

20. The method of claim 1 further comprising the step of selecting said polymeric material from the group consisting of polymers and copolymers of glycolide, lactide and polydiaxanone polydioxanone.

21. The method of claim 1 further comprising the step of causing said treatment strand to be echogenic.

22. The method of claim 1 further comprising the step of causing said treatment strand to have air bubbles dispensed within.

23. The method of claim 1 further comprising the step of selecting said polymeric material to yield a durometer in the range of about 20 to 40 once said polymeric material is solidified in said treatment strand.

24. The method of claim 1 further comprising the step of selecting the polymeric material to yield a durometer in the range of about 20–80 once solidified in said treatment strand.

25. The method of claim 1 further comprising the step of selecting the polymeric material that is moldable during manufacture of the therapeutic element.

26. The method of claim 1 further comprising forming said treatment strand by applying compression molding techniques on said polymeric material.

27. An improved method for manufacturing therapeutic elements by arranging a plurality of radioactive seed elements in a desired spacing for treatment of diseased tissue, the improvement comprising:

arranging the plurality of radioactive seed elements at desired space intervals according to a prescription treatment plan, without the use of spacers, wherein each of the plurality of radioactive seed elements has one of an indentation and a projection at a first end and one of an indentation and a projection at a second end;

flowing a liquid polymer into the space intervals between said plurality of radioactive seed elements and around said projections and indentations without completely encapsulating said radioactive seed elements; and allowing said liquid polymer to solidify to join said plurality of radioactive seed elements at said projections and indentations to form a treatment strand having axial rigidity and radial flexibility, and having said space intervals according to the prescription treatment plan.

28. A method of manufacturing therapeutic elements for treatment of a diseased tissue, the method comprising:

selecting a prescription treatment plan for treating the diseased tissue of a patient;

selecting a polymeric material;

selecting a species of radioactive seed element, said radioactive seed element having ends, said ends having one of an indentation and a projection;

positioning a plurality of said radioactive seed elements in an end-to-end orientation to create a desired spacing determined by said prescription treatment plan without using spacers;

flowing said polymeric material in a liquid form between and around the ends of the plurality of radioactive seed elements without completely encapsulating said radioactive seed elements; and allowing said liquid form of said polymeric material to solidify to form a treatment strand.

29. The method of claim 28 wherein the selecting a polymeric material step further includes selecting a biocompatible material.

30. The method of claim 28 wherein the selecting a polymeric material step further includes selecting a bio-absorbable material.

31. The method of claim 28 further comprising the step of incorporating a hormone into the polymeric material.

32. The method of claim 28 further comprising the step of incorporating a therapeutic agent into the polymeric material.

33. The method of claim 28 further comprising the step of incorporating a hormone into the plurality of radioactive seed elements.

34. The method of claim 28 further comprising the step of incorporating a therapeutic agent into the plurality of radioactive seed elements.

35. The method of claim 28 wherein the selecting a species of radioactive seed elements step further comprises selecting the species of radioactive seed elements from the group consisting of iodine 125, palladium 103, iridium 192, cesium 131, gold 198, yttrium 90, and phosphorus 32.

36. The method of claim 28 wherein the selecting the polymeric material step further comprises selecting the time of bio-absorption to substantially match the half-life of the species of radioactive seed elements.

37. The method of claim 28 further comprising the step of making the polymeric material echogenic.

38. The method claim 28 wherein the selecting the polymeric material step further comprises selecting the polymeric material to have a durometer range of about 20–80 after solidifying between and around the ends of the plurality of radioactive seed elements.

39. An improved method for manufacturing therapeutic elements by arranging a plurality of radioactive seed elements in a jig in a desired spacing for treatment of diseased tissue, the improvement comprising:

arranging in a jig a plurality of radioactive seed elements, said plurality of radioactive seed elements having a first end and a second end, wherein each first end has one of an indentation and a projection and each second end has one of the indentation and the projection;

positioning the plurality of seeds at desired space intervals according to a tissue treatment plan, said positioning step performed without use of spacers;

flowing a liquid polymer into the space intervals between said plurality of radioactive seed elements and around said projections and indentations of said radioactive seed elements without completely encapsulating said radioactive seed elements; and allowing said liquid polymer to solidify to join said plurality of radioactive seed elements at said ends in a treatment strand.

40. A method of manufacturing therapeutic elements for treatment of a diseased tissue, the method comprising:

selecting a prescription treatment plan for treating the diseased tissue of a patient;

selecting a polymeric material;

selecting a species of radioactive seed element;

obtaining a plurality of radioactive seed elements of said species of radioactive seed elements, each of said radioactive seed elements having a first end and a second end, wherein each said first end has one of an indentation and a projection and each said second end has one of an indentation and an projection;

positioning the plurality of said radioactive seed elements in a jig in an end-to-end orientation to create a desired spacing determined by said prescription treatment plan without the use of spacers;

flowing said polymeric material in a liquid form between and around the ends of the plurality of radioactive seed elements without completely encapsulating said radioactive seed elements; and allowing said liquid form of said polymeric material to solidify to form a treatment strand.

* * * * *